United States Patent

Bottaccio et al.

[11] 4,032,555
[45] June 28, 1977

[54] PROCESS FOR THE CARBOXYLATION OF ORGANIC SUBSTRATES WITH CARBON DIOXIDE

[75] Inventors: Giorgio Bottaccio; Gian Paolo Chiusoli; Enzo Alneri; Marcello Marchi; Giulio Lana, all of Novara, Italy

[73] Assignee: Montedison Fibre S.p.A., Milan, Italy

[22] Filed: Mar. 24, 1976

[21] Appl. No.: 670,010

[30] Foreign Application Priority Data

Mar. 28, 1975 Italy ................. 21816/75

[52] U.S. Cl. .............. 260/465 D; 260/475 SC; 260/515 R; 260/526 R; 260/537 R
[51] Int. Cl.² ............... C07C 51/15; C07C 59/32; C07C 59/36; C07C 121/66
[58] Field of Search ....... 260/465 D, 515 R, 526 R, 260/537 R, 475 SC

[56] References Cited

UNITED STATES PATENTS 3,595,907   7/1971   Patmore et al. ............... 260/515
3,658,874   4/1972   Patmore et al. ............... 260/465 D Primary Examiner—Dolph H. Torrence
Attorney, Agent, or Firm—Stevens, Davis, Miller & Mosher

[57] ABSTRACT

A process is disclosed for the carboxylation of organic substrates or reactants containing at least one active hydrogen atom by reaction with $CO_2$ and alkaline phenates in an organic medium, characterized in that the reaction is conducted in the presence of simple or substituted alkaline phenates in at least an aprotic medium which is at least a partial solvent for the phenate, and selected from the class consisting of cyclic ethers, aliphatic, cycloaliphatic and heterocyclic tertiary amines, and cyclic sulphones, and at temperatures between about 40° and 60° C. The alkaline phenate is selected from the class consisting of the Li, Na, K salts of the phenols of the general formula:

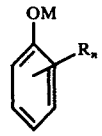

wherein R is hydrogen or an alkyl or an alkoxy group, linear or branched, having up to 20 carbon atoms, or a phenyl group, $n$ varies from 1 to 5, and M is the alkali metal. The starting organic substrate or reactant is selected from the class consisting of ketones, esters, nitroparaffins and nitriles. The alkaline phenate may be prepared "in situ" from the corresponding phenol and alkaline hydroxide with azeotropic elimination by means of solvent of the water thus formed.

5 Claims, No Drawings

PROCESS FOR THE CARBOXYLATION OF ORGANIC SUBSTRATES WITH CARBON DIOXIDE

The present invention relates to a process for the carboxylation of organic substrates.

More particularly, this invention relates to a process for the carboxylation of organic substrates containing atoms of active hydrogen through reaction with alkaline phenates and $CO_2$ in particular aprotic organic media having a solvent action.

The products thereby obtained offer important industrial applicative possibilities.

In particular, besides being valuable intermediates for organic syntheses, they may find particularly desirable uses in the fields of cosmetics, of solvents for cellulose acetate and nitrate, of resins, lacquers, inks, varnishes (benzoylacetic acid), of citric acid (beta-ketoglutaric acid), etc.

It is already known to carboxylate with $CO_2$ organic substrates having active hydrogen atoms, by reverting to the use of alkaline phenates in a dipolar solvent (N,N-dimethylformamide, dimethyl-sulphoxide, glimes, etc.) This, however, has the drawback of requiring the recovery of the dipolar solvent through technically laborious operations. Moreover, from the economics point of view, the use of a dipolar solvent involves an inordinate cost.

It is also known to carry out the same carboxylation in suspension employing organic hydrocarbon media, as well as in alkyl ethers, nitriles, anisole, etc., in the presence of phenates containing preferably in at least one ortho- position a sterically hindering group, such as for instance the ter-butyl group. But this method also shows certain disadvantages connected with yields and conversions that are not altogether satisfactory from the point of view of industrial application.

It has now been found (in accordance with the present invention) that the aforesaid carboxylation may be carried out with much better substrate conversions in comparison with those of the prior art, by operating in suitable aprotic solvents—either oxygenated or nitrogenated or possibly containing another ether atom.

It has been found that these improvements are achieved by using solvents having a C:O atomic ratio of between 1:1 and 5:1 and a C:N atomic ratio of between 3:1 and 10:1. The maximum number of C-atoms in the molecule of the solvent employed in carrying out the process according to the invention is 10.

Suitable oxygenated solvents belong to the group of linear and cyclic esters (e.g., ethyl acetate, propylene carbonate); of cyclic ethers (e.g., tetrahydrofurane, dioxane, tetrahydropyran); of the cyclic sulphones (e.g., sulpholane). Suitable nitrogeneous solvents belong to the class of tertiary amines of either open structure (e.g., triethylamine) or cyclic saturated structure (e.g., N-methylmorpholine) or heterocyclic structure (e.g., alkyl-pyridines such as picolines, 2-methyl-5-ethylpyridine, etc.)

The object of this invention is thus to provide a simple and economically attractive method for the carboxylation of organic substrates containing active hydrogen, by a reaction with alkaline phenates and $CO_2$, and one which is free of the drawbacks described in the prior art.

This and still other objects that will become even more apparent to those skilled in the art from the description that follows, are achieved according to this invention by a process for the carboxylation of organic substrates containing at least one atom of active hydrogen, by reaction with alkaline phenates and carbon dioxide in an organic medium, characterized in that the reaction is carried out in the presence of simple alkaline phenates or substituted alkaline phenates in at least an aprotic medium which is at least a partial solvent for the phenate, and which is selected from the class consisting of cyclic ethers, esters, aliphatic, cycloaliphatic and heterocyclic tertiary amines, and cyclic sulphones, at temperatures between 40° and 60° C.

In principle such solvents are characterized by a good, or at least fairly good, solubility with respect to the phenate used.

They may be cyclic ethers, preferably tetrahydrofurane, dioxane, tetrahydropyran; esters, preferably ethyl acetate and propylenecarbonate; aliphatic tertiary amines, preferably triethylamine; cycloaliphatic tertiary amines, preferably N-methylmorpholine; heterocyclic tertiary amines, preferably picolines, lutidines and 2-methyl-5-pyridine; or cyclic sulphones, preferably sulpholane.

For the desired carboxylation the alkaline phenates (Li, Na, K, etc.) are well suited, either simple or substituted, having the following general formula:

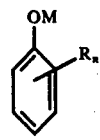

wherein R is hydrogen, an alkyl or an alkoxy group, linear or branched, having 1 to 20 carbon atoms, or a phenyl group. There may be present several R groups different from H and equal to or different from each other until exhaustion of the free phenol positions; i.e., n may vary from 1 to 5. M is an alkali metal.

Better results are obtained (in the order given) by the use of simple, substituted (e.g., cresolates) or sterically hindered phenates (e.g., ortho- and/or meta-tert.-butyl-phenates and cresolates, dodecylphenates), up to 2,6-di-tert-butyl-para-cresolate.

The alkali metal salt of phenate (Li, Na, K), in the case of solvents giving with water an azeotropic mixture and which are immiscible with it, such as for instance methylpyridines, may be prepared "in situ" from the corresponding phenol and the aqueous alkali metal hydroxide, by eliminating the $H_2O$ as an azeotropic mixture with an excess of the solvent itself. In the other cases it may be prepared separately, still by means of azeotropic methods, for instance by means of toluene, and then added to the carboxylation solvent in the dry state. These are pre se known techniques.

The carboxylizable organic substrates or reactants comprise all organic compounds containing at least one active hydrogen atom, for instance: ketones, esters, nitroparaffins, nitriles such as acetophenone, acetone, phenylacetonitrile, nitromethane, methyl phenyl acetate, etc.

The reaction is conducted preferably using from 1 to 4 mols of alkaline phenate per mol of organic substrate or reactant.

By using a 1:1 ratio between the alkaline phenate and the substrate or reactant to be carboxylated, and by operating at room temperature, conversions are not so high although the selectivity still remains high inasmuch as the substrate or reactant is for the most part readily recovered.

Better conversions are achieved by increasing the above-mentioned molar ratio and/or the reaction temperature.

In fact, a particularly desirable aspect of this carboxylation technique is operation at a temperature around 50° C. Under such conditions, and at atmospheric pressure, the Kolbe reaction (introduction of a carboxylic group into the phenate nucleus itself), contrary to what happens with dipolar aprotic solvents, is reduced to a minimum in the case of unsubstituted phenate and of the cresolates (less than 1% with respect to the phenate used) and is practically nonexistent in the case of o-tert-butyl-p-cresolate which still has an available ortho-position.

The reaction may be conducted, depending on the reactants, at a temperature between 40° and 60° C, but preferably at about 50° C.

According to a typical embodiment, the reaction is carried out in the following way: To a solution of phenate in the solvent, preliminarily saturated with carbon dioxide, under stirring and at about 50° C, there is additionated the substrate or reactant to be carboxylated, in a ratio varying from 1 to 4 mols of phenate per mol of pre-established substrate. The mixture is kept under stirring at the indicated temperature in a $CO_2$ atmosphere unitl completion of the reaction.

The products are then isolated and purified according to per se known techniques. For instance, in the case of the use of acetone, under vigorous stirring, there is added a quantity of $H_2O$ which is equimolar with respect to the phenate. The alkaline salts of the acetoacetic and 3-ketoglutaric acids produced, together with the sodium bicarbonate resulting from the phenate excess, percipitate in a crystalline form easily filtered and washed. The acid may be freed from the salt by per se known techniques, for instance by acidification with a mineral acid followed by extraction with ethyl ether.

In the case of other substrates or reactants, the reaction mixture is diluted with an equal volume of $H_2O$, in the presence of $CO_2$, then the phenol, the solvent and the unreacted substrate are extracted by means of ether, while the aqueous phase is acidified and the acid recovered for further extraction with ether.

The process of the present invention, due to the mild operating conditions, shows specific advantages that may thus be summarized:

a. in comparison with the use of the hydrocarbon reaction media of the prior art:
much higher conversions and selectivity;
greater solubilities of the reactants and, thus, lower reaction volumes;
absence of condensation byproducts of the substrate or reactant (e.g., mesityl oxide in the case of acetone);
possibility of using phenates of lower cost in comparison to the hindered phenates.

b. in comparison with the use of dipolar aprotic solvents:
higher conversions and selectivity;
greater stability of the solvent, which allows its recovery through technically less burdensome operations;
in general, a lower cost for the solvents;
a lesser formation (or the substantially complete absence) of byproducts of carboxylation of the phenate.

The invention will now be described in still greater detail via following examples given for purely illustrative purposes.

The examples reported in the table below, for the sake of brevity, include abbreviations which are as follows:

THF = tetrahydrofurane;
MEP = 2-methyl-5-ethylpyridine.

Moreover, by the term "conversion of the substrate to acid %" is meant the molar percentage of substrate or reactant converted to the corresponding acid. Thus, benzoyl acetic acid will be obtained from acetophenone; acetoacetic acid (monocarboxylate) or 3-ketoglutaric acid (dicarboxylate) will be obtained from acetone; semi-nitrile of phenylmalonic acid will be obtained from phenyl-acetonitrile; and semi-ester of phenylmalonic acid will be obtained from the methyl-phenyl acetate.

Finally, Examples 36 to 40 are given to demonstrate the advantages of the present invention in comparison to the known reaction technique carried out in suspension.

The examples were carried out according to the following common scheme:

To the sodium phenate solution in the designated solvent preliminarily saturated with carbon dioxide, and under stirring at the stated temperature, the substrate or reactant to be carboxylated was added in the ratio indicated in the table. This reaction mixture was then stirred in a carbon dioxide atmosphere until the reaction was completed. At this point, in the case of acetone, there was added under vigorous stirring a quantity of $H_2O$ equimolar with respect to the starting phenate.

The sodium salts of the acetoacetic and 3-keto-glutaric acids thus produced, together with the sodium bicarbonate derived from the excess of phenate, precipitate in a crystalline form and were then filtered and washed with a solvent (benzene, petroleum ether, chloroform, etc.)

The acid was then freed from the salt by means of per se known techniques by acidification with dilute sulphuric acid, followed by extraction with ethyl ether.

In the case of the other substrates or reactants, the reaction mixture was diluted with an equal volume of $H_2O$ in the presence of $CO_2$. The phenol, the solvent, and the remaining unreacted substrate or reactant were then extracted with ether, the aqueous phase was acidified, and the acid recovered by further extraction with ether.

The data for the various examples are given in the subjoined table:

TABLE

| | Substrate | Solvent | Phenol (Sodium Salt) | Temperature °C. | Molar Ratio Phenate to Substrate | Concentration Phenate | Time Hours | Conversion to Dicarboxylic Acid Mol % | Conversion to Monocarboxylic Acid Mol % | Conversion to Acid Mol % |
|---|---|---|---|---|---|---|---|---|---|---|
| 1 | Acetophenone | THF | 2-terbutylphenol | 25 | 1:1 | 2N | 3 | | | 46 |
| 2 | Acetophenone | THF | 2-terbutylphenol | 25 | 4:1 | 2N | 3 | | | 92 |
| 3 | Acetophenone | THF | 2-terbutylphenol | 50 | 1:1 | 2N | 3 | | | 47.6 |
| 4 | Acetophenone | THF | 2-terbutylphenol | 50 | 4:1 | 2N | 3 | | | 97 |
| 5 | Acetophenone | THF | Phenol | 25 | 1:1 | 2N | 3 | | | 23.2 |
| 6 | Acetophenone | THF | Phenol | 25 | 4:1 | 2N | 3 | | | 32 |
| 7 | Acetophenone | THF | Phenol | 50 | 1:1 | 2N | 3 | | | 30.5 |
| 8 | Acetophenone | THF | Phenol | 50 | 4:1 | 2N | 3 | | | 89 |
| 9 | Acetophenone | THF | m-cresol | 50 | 1:1 | 2N | 3 | | | 35.9 |
| 10 | Acetophenone | THF | 0-hydroxyanisole | 50 | 4:1 | 2N | 3 | | | 12 |
| 11 | Acetophenone | propylenecarb. | 2-terbutylphenol | 50 | 4:1 | 2N | 3 | | | 83 |
| 12 | Acetophenone | triethylamine | 2-terbutylphenol | 50 | 4:1 | 2N | 3 | | | 94.5 |
| 13 | Acetophenone | N-methylmorpholine | 2-terbutylphenol | 50 | 4:1 | 2N | 3 | | | 84 |
| 14 | Acetophenone | sulpholane | 2-terbutylphenol | 50 | 4:1 | 2N | 3 | | | 91 |
| 15 | Acetone | THF | 2-terbutylphenol | 25 | 4:1 | 2N | 3 | 46. | 31.8 | |
| 16 | Acetone | THF | 2-terbutylphenol | 50 | 4:1 | 2N | 3 | 83.7 | 16.3 | |
| 17 | (°) Acetone | THF | phenol | 50 | 4:1 | 2N | 3 | 47.9 | 10.2 | |
| 18 | Acetone | THF | 2-terbutyl p.cresol | 50 | 4:1 | 2N | 3 | 86.7 | 13 | |
| 19 | Acetone | Dioxane | 2-terbutylphenol | 50 | 4:1 | 2N | 3 | 78 | 10 | |
| 20 | Acetone | Ethyl acetate | 2-terbutylphenol | 50 | 4:1 | 2N | 3 | 77.6 | 18 | |
| 21 | Acetone | Ethyl acetate | 2-terbutyl p.cresol | 50 | 4:1 | 2N | 3 | 79.8 | 14.9 | |
| 22 | Acetone | β-picoline | phenol | 50 | 4:1 | 2N | 3 | 76.4 | 14.7 | |
| 23 | Acetone | β-picoline | 2-terbutylphenol | 50 | 4:1 | 2N | 3 | 85.5 | 14.2 | |
| 24 | Acetone | β-picoline | metacresol | 50 | 4:1 | 2N | 3 | 66 | 13.7 | |
| 25 | (°) Acetone | MEP | phenol | 50 | 4:1 | 2N | 3 | 60.5 | 13.7 | |
| 26 | Acetone | MEP | ortho-cresol | 50 | 4:1 | 2N | 3 | 69 | 19.4 | |
| 27 | Acetone | MEP | 2-terbutylphenol | 50 | 4:1 | 2N | 3 | 83.8 | 15.4 | |
| 28 | Acetone | MEP | 2-terbutyl p.cresol | 50 | 4:1 | 2N | 3 | 82.2 | 17.6 | |
| 29 | Acetone | MEP | m-cresol | 50 | 4:1 | 2N | 3 | 65.5 | 15.0 | |
| 30 | Acetone | MEP | p-cresol | 50 | 4:1 | 2N | 3 | 62.5 | 14.9 | |
| 31 | Phenylacetonitrile | THF | 2-terbutylphenol | 50 | 4:1 | 2N | 3 | | | 99 |
| 32 | Phenolacetonitrile | THF | phenol | 50 | 4:1 | 2N | 3 | | | 42.9 |
| 33 | Methyl phenylacetate | THF | 2-terbutylphenol | 50 | 4:1 | 2N | 3 | | | 66.5 |
| 34 | Methyl phenylacetate | THF | phenol | 50 | 4:1 | 2N | 3 | | | 21.4 |
| 35 | Nitromethane | THF | 2-terbutyl p.cresol | 50 | 4:1 | 2N | 3 | | | 52 |
| 36 | Acetone | acetonitrile | 2-terbutylphenol | 50 | 4:1 | 2N | 3 | 27.4 | 3.8 | |
| 37 | Acetone | nitrobenzene | 2-terbutylphenol | 50 | 4:1 | 2N | 3 | 30.1 | 4.2 | |
| 38 | Acetone | diisopropylether | 2-terbutylphenol | 50 | 4:1 | 2N | 3 | 32.9 | 4.6 | |
| 39 | Acetone | anisole | 2-terbutylphenol | 50 | 4:1 | 2N | 3 | 26 | 3.6 | |
| 40 | Acetone | diphenylether | 2-terbutylphenol | 50 | 4:1 | 2N | 3 | 21.9 | 3.1 | |

(°) 17 = Salicylic acid/phenol 0.004%
(°) 25 = Salicylic acid/phenol 0.15%

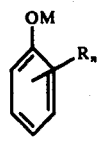

What is claimed is:

1. A process for the carboxylation of organic substrates or reactants containing at least one active hydrogen atom, and selected from the class consisting of ketones, esters, nitroparaffins and nitriles, by reaction with $CO_2$ and alkaline phenates in an organic medium, characterized in that the reaction is conducted in the presence of an alkaline phenate in an organic medium which is at least a partial solvent for the phenate, and selected from the class consisting of tetrahydrofurane, dioxane, tetrahydropyran, ethyl acetate, propylenecarbonate, triethylamine, N-methylmorpholine, a picoline, a lutidine, 2-methyl-5-ethyl-pyridine, and sulpholane, and at a temperature between about 40° and 60° C; the alkaline phenate being selected from the class consisting of the Li, Na, K salts of phenols of the general formula:

wherein R is hydrogen or an alkyl or an alkoxy group, linear or branched, having up to 20 carbon atoms, or a phenyl group, $n$ varies from 1 to 5, and M is Li, Na or K.

2. A process according to claim 1, wherein the alkaline phenate is sodium ortho-tert-butyl-para-cresolate.

3. A process according to claim 1, wherein the process is carried out at a temperature of about 50° C.

4. A process according to claim 1, wherein for each mol of substrate or reactant there are used from 1 to 4 mols of alkaline phenate.

5. A process according to claim 1, wherein the alkaline phenate is prepared "in situ" from the corresponding phenol and alkaline hydroxide with azeotropic elimination by means of solvent of the water thus formed.